United States Patent [19]
Ziegler et al.

[11] Patent Number: 5,456,673
[45] Date of Patent: Oct. 10, 1995

[54] LOCKING CANNULA FOR ENDOSCOPIC SURGERY

[75] Inventors: Mark W. Ziegler, Sunnyvale; Larry J. Voss, San Jose, both of Calif.

[73] Assignee: Stryker Corporation, Kalamazoo, Mich.

[21] Appl. No.: 216,813

[22] Filed: Mar. 23, 1994

[51] Int. Cl.[6] ....................................................... A61M 5/00
[52] U.S. Cl. ............................ 604/264; 604/283; 600/104
[58] Field of Search ..................................... 604/264, 280, 604/283, 905, 164–169; 606/184, 185; 128/4

[56] References Cited

U.S. PATENT DOCUMENTS

| | | |
|---|---|---|
| 4,586,496 | 5/1986 | Keller . |
| 4,589,414 | 5/1986 | Yoshida et al. . |
| 4,697,586 | 10/1987 | Gazale . |
| 4,798,213 | 1/1989 | Doppelt . |
| 5,171,245 | 12/1992 | Cezana . |
| 5,312,351 | 5/1994 | Gerrone .................... 604/264 X |
| 5,318,585 | 6/1994 | Guy et al. ................. 604/264 X |
| 5,347,988 | 9/1994 | Hori ............................. 128/4 |
| 5,368,014 | 11/1994 | Anapliotis et al. ................ 128/4 |

FOREIGN PATENT DOCUMENTS

238724A1  9/1986  Germany .

OTHER PUBLICATIONS

FIGS. 1 and 2, partially broken and central cross–sectional view (1 sheet).
FIGS. 3 and 4, side elevational and central cross–sectional view (1 sheet).
FIGS. 1–4 and sketches 1–3 showing Stryker Model 34–30–112, 158 Trocar/Cannula on sale in US before Mar. 23, 1993.

*Primary Examiner*—John D. Yasko
*Attorney, Agent, or Firm*—Flynn, Thiel, Boutell & Tanis

[57] ABSTRACT

An endoscopic surgery cannula insertable into a surgical site in a patient for coaxially slideably receiving an endoscopic surgical tool. The cannula comprises a distal portion insertable into the surgical site. The cannula further comprises a proximal portion accessible to surgical personnel for receiving an endoscopic surgical tool and having a passage through which the distal portion of the surgical tool can be brought into the surgical site. The cannula proximal portion comprises a lock mechanism transversely slidable for interfering with axial movement with the tool therein and elastomeric loop structure stretchable for resiliently urging the lock mechanism transversely on the cannula to a lock position retaining the surgical tool in the cannula and which may be resiliently overcome to permit removal of the tool from the cannula.

12 Claims, 6 Drawing Sheets

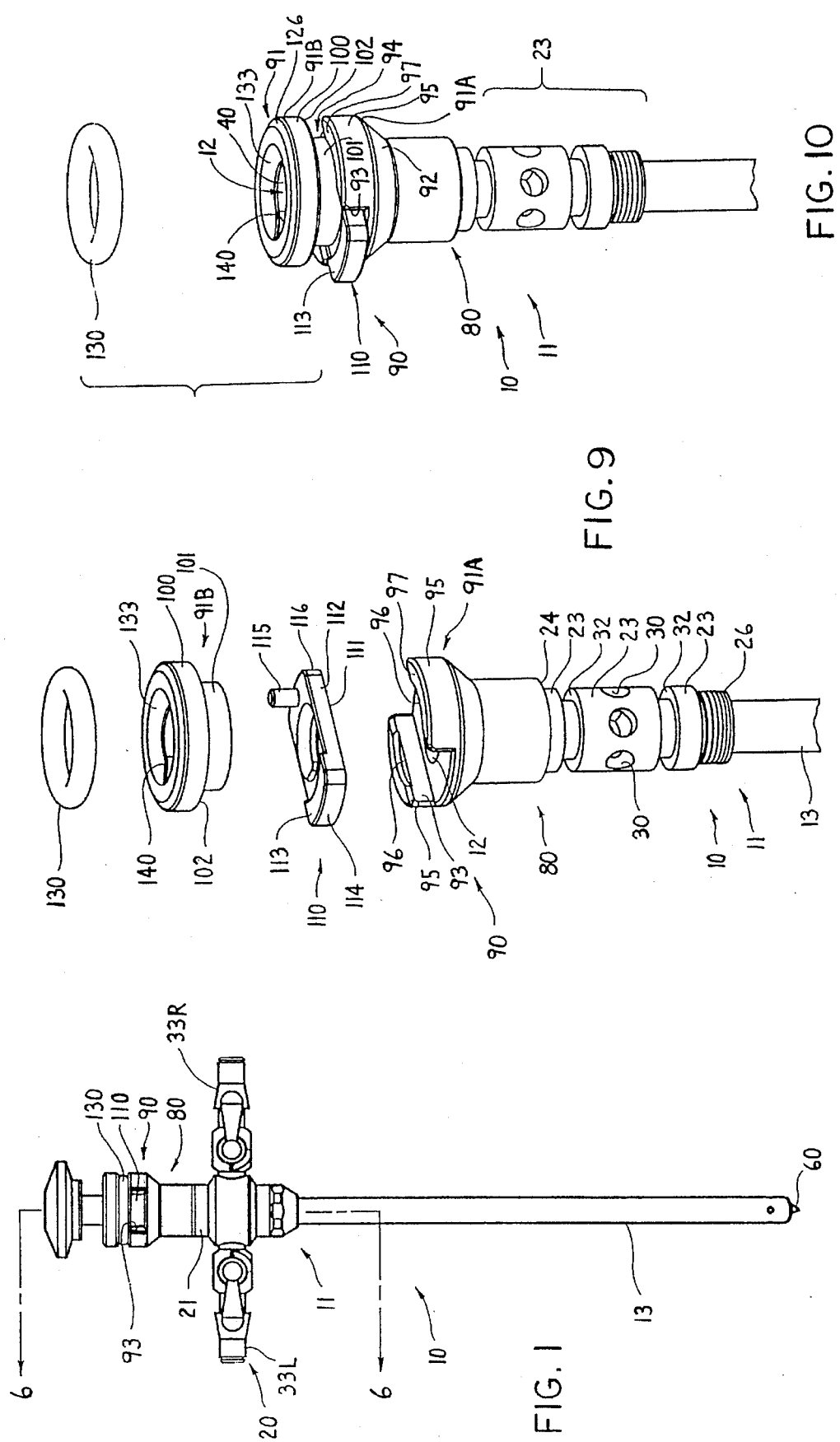

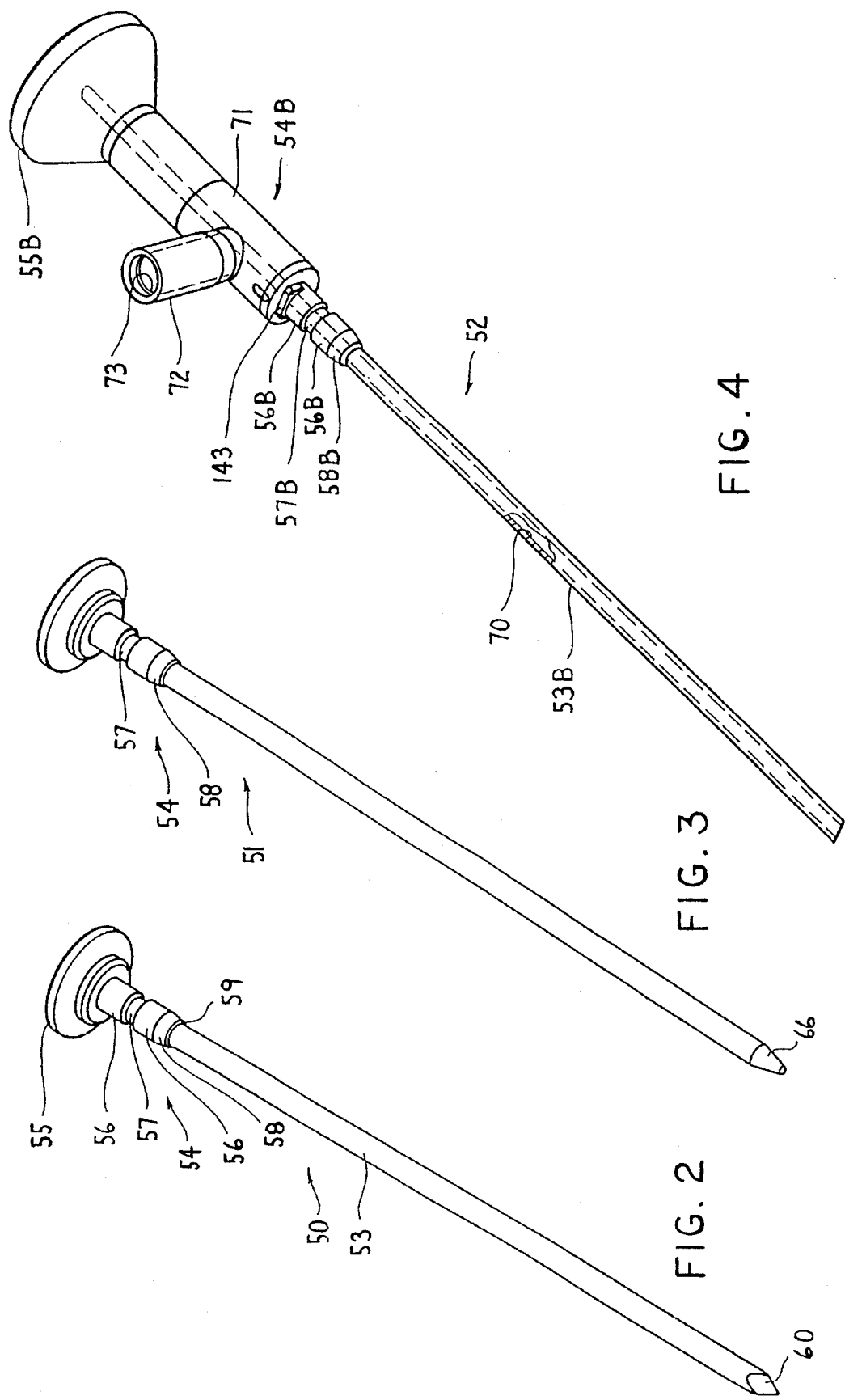

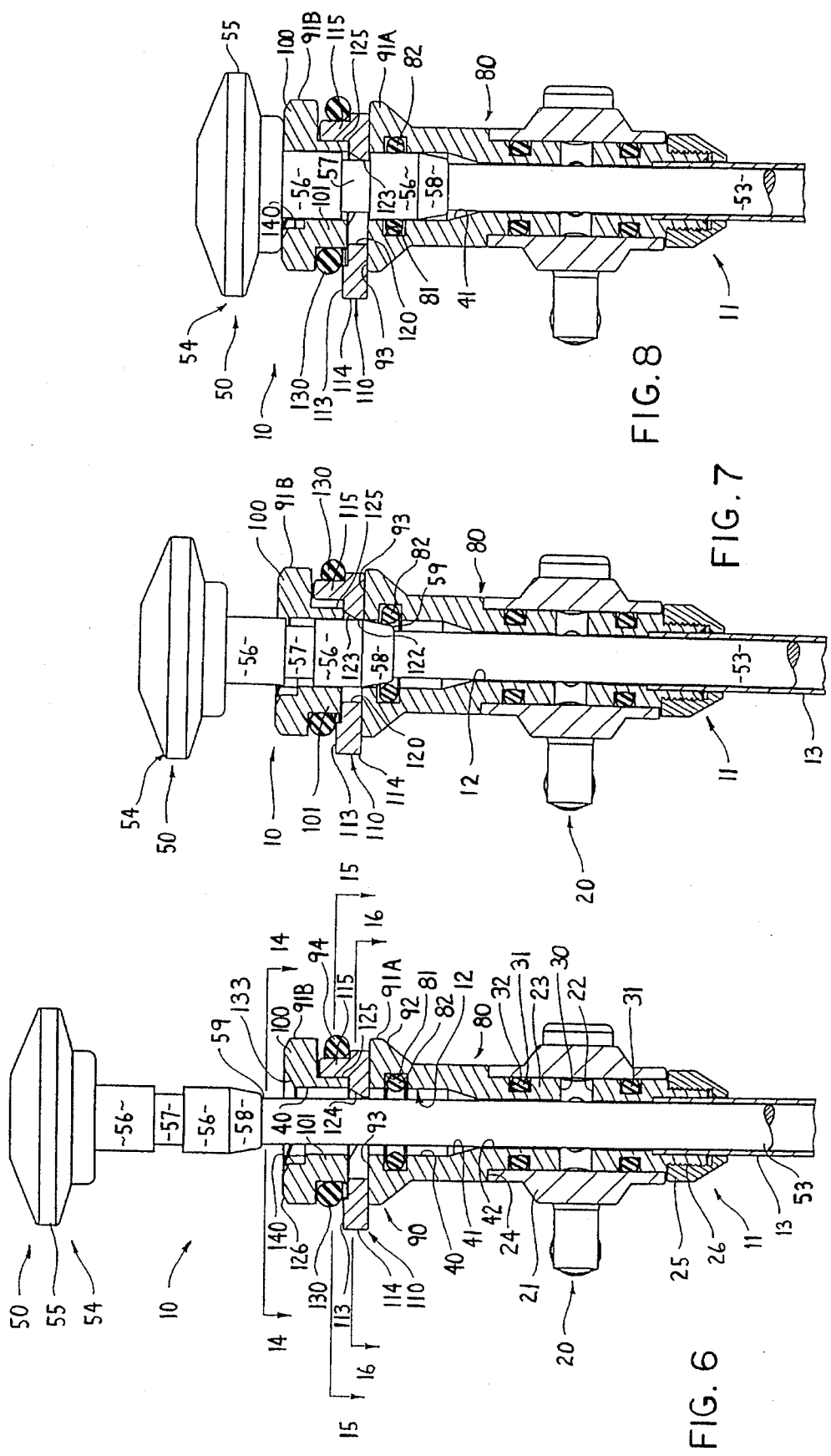

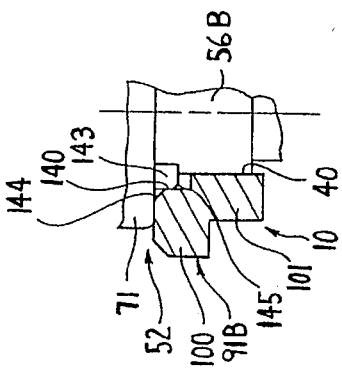
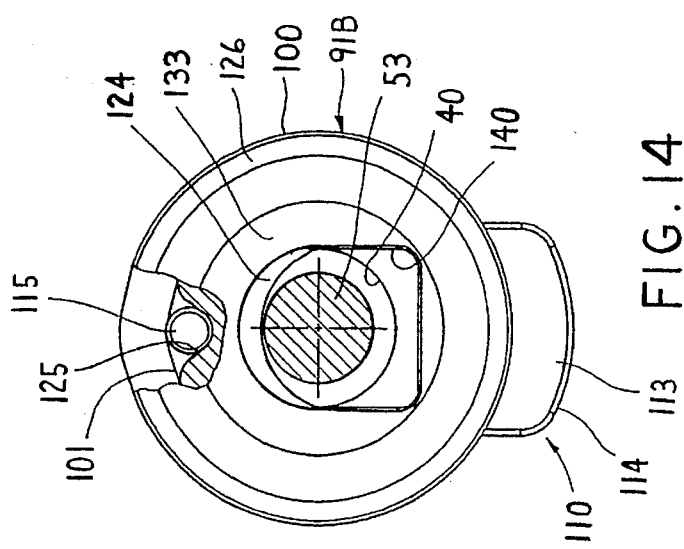
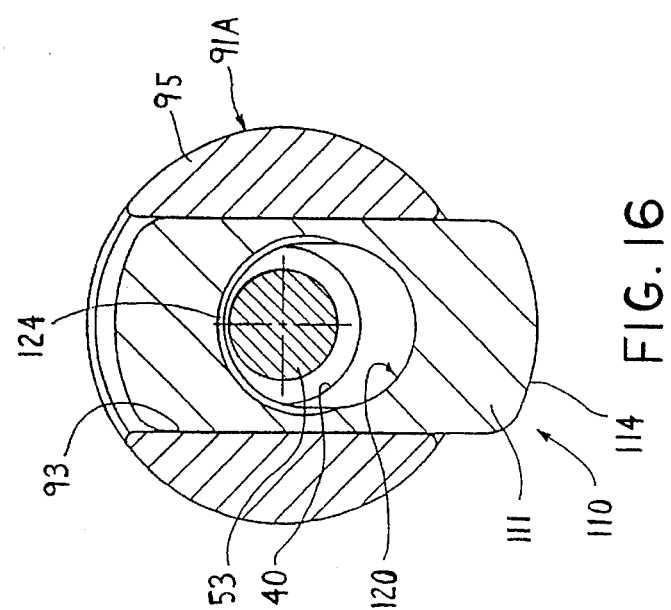

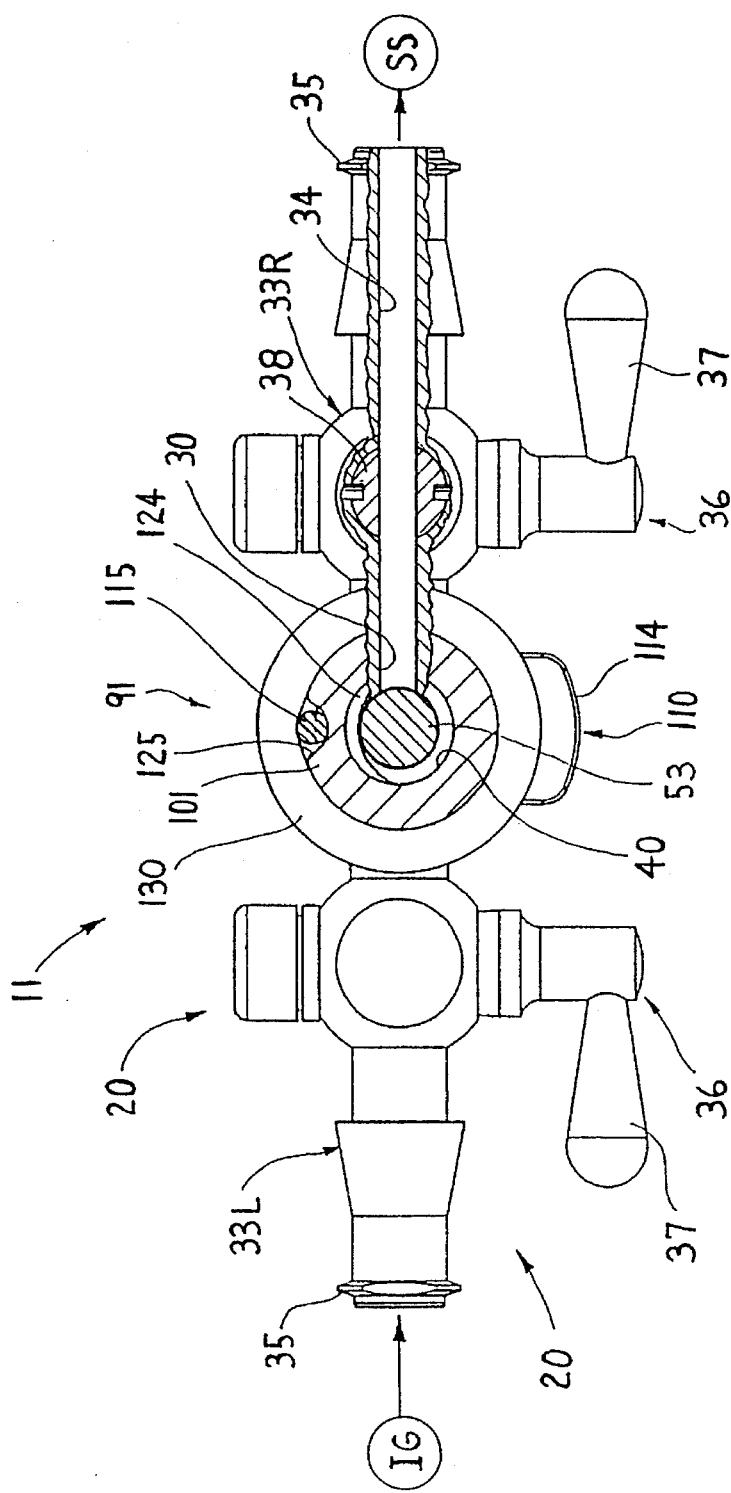
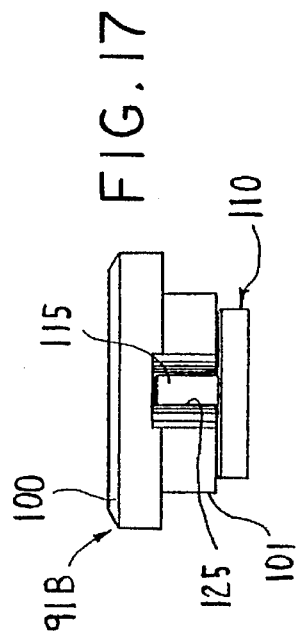

LOCKING CANNULA FOR ENDOSCOPIC SURGERY

FIELD OF THE INVENTION

This invention relates to an endoscopic surgical instrument system and more particularly to such a system including a locking cannula.

BACKGROUND OF THE INVENTION

It has been known in arthroscopic surgical procedures, to enter a surgical site, for example a knee joint, with an elongate entry tool, such as a trocar, sheathed in a snug fitting outer cannula. Thereafter the entry tool is removed, leaving the entry end of the cannula at the surgical site and the other end of the cannula protruding from the patient. Thereafter, one or more additional elongate surgical tools, such as an arthroscope or obturator can, in desired sequence, be alternately inserted through the cannula to reach the surgical site.

Further, it is known to equip the cannula for connection to an irrigation liquid source for injection of irrigation liquid therethrough into the surgical site, or to a pressure gas source for creating an inflated chamber at the surgical site, or to a suction source for removing flowable material from the surgical site.

In each instance, the cannula extending into the surgical site acts as a conduit of access to the surgical site from outside the body in the patient and permits a variety of surgical procedures to be performed without requiring more than the very small incision needed to insert the distal end of the cannula.

In prior devices of this type, the outer end of the cannula may be provided with a manually actual locking device engageable with a connector on the tool for axially fixing the tool within the sleeve.

In one such prior locking device, a threaded member must be rotated with respect to the rest of the cannula to lock and unlock a tool with respect to the cannula. However, some surgeons have confused the lock and unlock rotation directions. Further, the threaded member have become slippery during surgery and require extra care to lock and unlock. Further, a surgeon may fail to fully rotate the threaded member and thus need to repeat the rotation. It may be difficult to achieve locking and unlocking with one hand.

In a subsequent prior art device, namely one shown in U.S. Pat. No. 5,171,245 assigned to the Assignee of the present invention, locking and unlocking may be achieved with one hand. However, the locking mechanism is relatively complex structurally and hence expensive to produce.

Accordingly, in a continuing effort to improve on apparatus of this general kind, the present invention was developed.

Accordingly, the objects and purposes of this invention include provision of such an improved locking cannula and tool arrangement.

Further objects and purposes of the invention will be apparent to persons acquainted with apparatus of this general type upon reading the following specification and inspecting the accompanying drawings.

SUMMARY OF THE INVENTION

An endoscopic surgery cannula insertable into a surgical site in a patient for coaxially slideably receiving an endoscopic surgical tool. The cannula comprises a distal portion insertable into the surgical site. The cannula further comprises a proximal portion accessible to surgical personnel for receiving an endoscopic surgical tool and having a passage through which the distal portion of the surgical tool can be brought into the surgical site. The cannula proximal portion comprises a lock mechanism transversely slidable for interfering with axial movement with the tool therein and elastomeric loop structure stretchable for resiliently urging the lock mechanism transversely on the cannula to a lock position retaining the surgical tool in the cannula and which may be resiliently overcome to permit removal of the tool from the cannula.

BRIEF DESCRIPTION OF THE DRAWINGS

FIG. 1 is a front elevational view of a cannula embodying the invention, with a trocar inserted therein.

FIG. 2 is a pictorial view of the trocar of FIG. 1.

FIG. 3 is a pictorial view of an obturator insertable in the FIG. 1 cannula in place of the trocar.

FIG. 4 is a partially broken pictorial view of a scope member substitutable in the FIG. 1 cannula for the trocar.

FIG. 6 is a fragmentary enlarged central cross-sectional view substantially taken on the line 6—6 of FIG. 1, and showing a tool, such as the FIG. 2 trocar, partially inserted in the cannula.

FIG. 7 is a view similar to FIG. 6 with the tool inserted far enough in the cannula to displace the lock slide.

FIG. 8 is a view similar to FIG. 7 but with the tool fully inserted in the cannula.

FIG. 8A is a fragment of FIG. 8 showing the circumferential locator notch of FIG. 8 occupied by the key of the FIG. 4 tool.

FIG. 9 is a fragmentary exploded view of the FIG. 1 cannula with the locking unit exploded.

FIG. 10 is a fragmentary view of the FIG. 1 cannula with the locking unit assembled except for showing the O-ring in exploded relation thereto.

FIG. 14 is a partially broken top view of the locking unit substantially taken on the line 14—14 of FIG. 6.

FIG. 15 is a partially broken sectional view substantially taken on the line 15—15 of FIG. 6 and showing the FIG. 1 valve unit.

FIG. 16 is a sectional view substantially taken on the line 16—16 of FIG. 6.

FIG. 17 is a fragmentary elevational view of the slider post and annular cap as taken from the right in FIG. 8, but with the O-ring absent.

DETAILED DESCRIPTION

Figure 5:
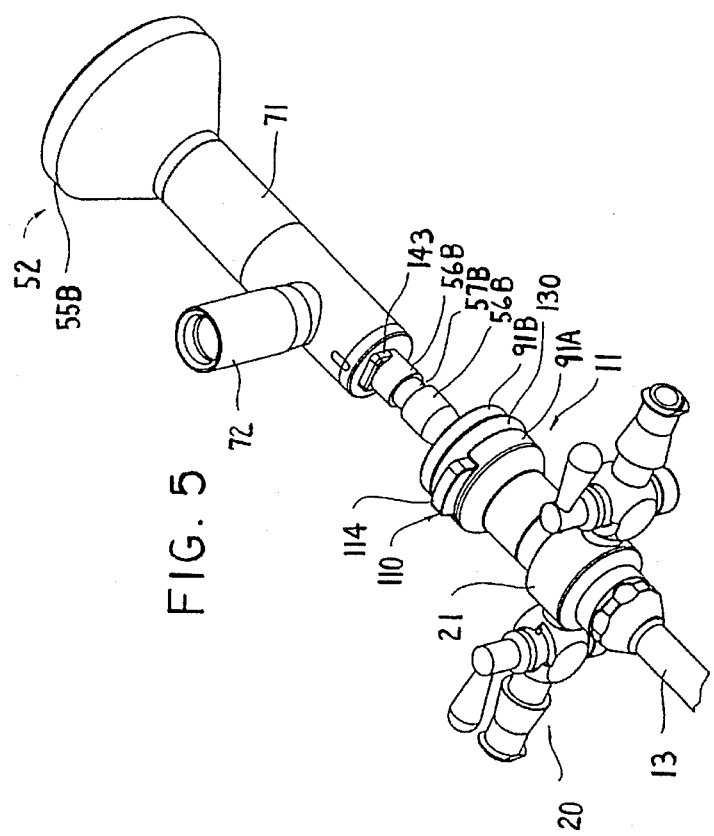
FIG. 5 is a fragmentary pictorial view of the FIG. 1 cannula with the FIG. 4 scope member partly inserted therein.

A cannula 10 comprises a proximal (near or upper in FIG. 1), elongate, hollow, generally tubular head 11 (FIGS. 1, 7 and 9) having a coaxial central passage 12 (FIG. 7). An elongate tube 13 is coaxially fixedly recessed at its upper end (FIG. 7) in the lower end portion of the passage 12 and extends dependently from the head 11 to form the distal (far or in the drawings lower) portion of the cannula 10. The head and tube may be fixed together by any convenient means such as laser welding. The tube 13 has a central passage 14 which is of the same diameter as, and constitutes a flush coaxial extension of, the central passage 12 of the head 11.

In the embodiment shown, the head 11 carries a valve unit 20 (FIGS. 1 and 6). The valve unit 20 has a central hub 21 fixed on and in fluid communication with the lower portion 23 of the head 11. The central hub 21 (FIG. 6) has a coaxial, cylindrical, longitudinal bore 22 for snugly coaxially sleeving over the reduced diameter, substantially cylindrical lower portion (or shank) 23 of the head 11. The valve unit hub 21 is axially fixed on the head 11, here by axial sandwiching between a downward facing step 24 of the head 11 at the top of the shank 23 and a nut 25 coaxially threaded on a reduced diameter externally threaded depending extension 26 of the head lower portion 23. The shank 23 of the head 11 has plural (FIG. 6), evenly circumferentially spaced, radial holes 30 (FIGS. 6 and 9) communicating between the central passage 12 of the head 11 and the bore 22 of the valve unit hub 21 for fluid communication therebetween. Annular seals, here O-rings 31 are seated in annular grooves 32 (FIGS. 6 and 9) spaced axially above and below the radial holes 30 and facing radially outward in the periphery of the shank 23. The O-rings 31 seal against the surface of the bore 22 of the hub 21 to prevent fluid leakage between the radial holes 30 and the atmosphere surrounding the cannula 10. The valve unit 20 further includes left and right fluid conduits 33L and 33R (FIGS. 1 and 15) extending diametrally from the hub 21 and each having a fluid passage 34 (FIG. 15) extending radially through the hub 21 into communication with the central passage 12 in the head 11. The outer ends of the fluid passages 34 open outward through the radially outer ends of the left and right conduits 33L and 33R. The outer ends 35 of the conduits 33L and 33R are conventionally connectable, as through suitable resilient tubing not shown to, for example, a conventional inflation gas source IG, a conventional suction source SS, or another desired fluid source, such as a source of irrigation liquid.

The fluid conduits 33L and 33R each include a conventional stopcock, or on/off valve, 36. The valves 36 may be of variable opening size to modulate the flow of fluid therethrough. In the embodiment shown, each valve 36 comprises a manually actuable valve handle 37 rotatable to rotate a corresponding rotatable valve element 38 (FIG. 15) in a conventional matter.

The central passage 12 in the head 11 includes an enlarged upper portion 40 (FIG. 6), a narrowed lower portion 42 (here communicating with the radial holes 30 above-mentioned), and a downward tapered, generally frustoconical portion 41 joining the upper and lower portions 40 and 42.

Examples of tools useable with the FIG. 1 cannula 10 are shown at 50, 51 and 52 in FIGS. 2, 3 and 4 respectively.

Thus, for example, the tool 50 (FIG. 2) comprises a trocar including an elongate rod 53 snugly axially slidable in the narrowed lower portion 42 of the cannula head central passage 12 (as seen in FIG. 6). The tool 50 further includes a proximal portion 54 (FIGS. 2 and 6) coaxially fixed atop the rod 53. The proximal portion 54 comprises, starting at the top, a radially enlarged handgrip 55 and a generally cylindrical intermediate diameter portion 56 coaxially connecting the handgrip 55 to the top of the rod 53. The intermediate diameter portion 56 has, spaced between its ends, an annular lock groove 57. The intermediate diameter portion 56 tapers downward at 58 toward the top of the rod 53. In the embodiment shown, the taper 58 does not merge into the top of the rod 53 but rather joins it by means of a short radial step 59. The bottom end 60 of the trocar 54 is pointed as indicated in FIG. 2.

The trocar 54 is insertable into the cannula 10 in a distal (downward in the drawings) direction, as indicated by the insertion sequence at FIGS. 6–8, to achieve the installed position shown in FIG. 1, generally as follows. More particularly the pointed bottom end 60 of the trocar 54 is inserted downward into the top of the central passage 12 of the cannula 10, passing downward through the head 11 and tube 13 to emerge, as shown in FIG. 1 at the lower end tube 13. Toward the end of this insertion, the taper 58 and locking groove 57 enter the top portion of the cannula central passage 12, as indicated in FIGS. 7 and 8. Protrusion of the bottom end 60 of the trocar distally from a bottom end of the tube 13 enables it to pierce patient tissue thereby allow insertion of the distal end portion of the cannula through such patient tissue to such an internal operating site (not shown).

In a typical surgical sequence, the trocar 50 may thereafter be withdrawn upward from the cannula (in a reversal of the FIG. 6–8 sequence) and another tool, such as the FIG. 3 obturator 51, may be inserted downward into the cannula 10 in place of the trocar 50. The obturator 51 is similar to the trocar 50 except for having a blunt bottom end or nose 66, which may be useful in more gently parting tissue in the last stage of insertion of the cannula into the surgical site.

Thereafter, the obturator 51 is removable from the cannula 10 and may be replaced by a further tool, for example the scope device 52 shown in FIG. 4. The scope device 52 here shown is generally similar to the trocar 50 except that it is hollow from end to end, as defined by a central bore, a portion of which is rather schematically indicated at 70. Further, the proximal portion 54B is elongated by coaxial insertion of a hollow, generally tubular, viewing barrel 71 between the intermediate diameter portion 56B and the handgrip 55B. The handgrip 55B may thus also serve as a cheek or brow rest for the surgical team member whereby such surgical team member can look down the central bore 70, the full length of the scope device 52 and into the surgical site. The central bore 70 may house optical elements (e.g. lenses) not shown. The distal (bottom in FIG. 4) end of the tube 53B is typically closed against fluid flow by a window not shown. Further, the scope device 52 here includes a hollow, tubular, radially outward extending fitting 72 having a central through opening 73 communicating with the central bore 70 for further accessory use. The scope device 52 may be used for direct vision into the surgical site by a surgical team member, as above-mentioned, or may be used to mount a camera, such as a television camera, to enable pictorial display of the surgical site on a television screen (not shown) visible to the surgical team.

As above suggested, the scope device 52 is insertable into the top of the cannula 10 in substitution for other tools, including the above described FIG. 2 trocar 50 and FIG. 3 obturator 51.

To the extent above-described, the apparatus may be conventional.

Turning now to structure more specifically concerned with the present invention, attention is directed to FIGS. 9 and 10. The head 11 includes an upper portion (proximal portion) 80 extending upward from the step 24 (FIG. 6) and which includes an upper portion 40 and a downward tapered portion 41 of the head central passage 12. An annular groove 81 (FIG. 6) coaxially indents the upper portion 40 of the central passage 12 of the head 11 above the downward tapered portion 41. An elastomeric seal, here an O-ring, 82 is housed in, and projects somewhat radially inward from the annular groove 81 (FIG. 6).

In the tools 50–52 here shown, the bottom step 59 is rounded as seen for example in FIG. 6. Upon insertion of such a tool (e.g. the tool 50), into the open proximal end of the central passage 12, the rounded bottom step 59 of the taper 58 moves easily down past the O-ring 82 without risk of damage to the O-ring, as seen in FIG. 7. The taper 58 guides the overlying intermediate diameter portion 56 of the tool 50 forward into surrounded, snug sealed contact with the interior of the O-ring 82 as the handgrip 55 of the tool 50 comes to rest atop the proximal end of the cannula 10 as seen in FIG. 8. The resulting, circumferentially continuous, resilient, radial pressure seal between the O-ring 82 and the cylindrical intermediate diameter portion 56 of the tool 50 prevents escape of fluid, particularly gas under pressure, from a surgical site (not shown) at the distal end of the cannula 10. In particular, the radial compression of the cross-section of the O-ring 82 between the tool portion 56 and the surrounding proximal portion 80 of the cannula head 11 positively blocks axial fluid flow past the O-ring 82. This gas seal, provided by the O-ring 82 and tool portion 56, does not require close tolerance machining, is provided relatively inexpensively, provides a reliable seal, and is thus an advantageous improvement over prior gas seals achieved by seating contact of opposed tapers on the tool and in the central passage of the cannula (like the tapers 58 and 41 of FIG. 8 if suitably axially relocated).

A lock unit 90 (FIGS. 6, 9 and 10) includes a lock carrier 91 which constitutes the upper part of the proximal portion 80 of the head 11. The carrier 91 lies above the O-ring 82 as seen in FIG. 6. The lock carrier 91 is preferably radially enlarged and integrally connected to the reduced lower diameter portion of the proximal portion 80 by an exterior taper 92. The carrier 91 (FIG. 10) comprises a transverse (here diametral) guideway 93 of generally rectangular cross-section spaced close above the taper 92 and an annular groove 94 above the transverse guideway 93.

The portion of the head 11 defining the carrier 91 is formed of two pieces, namely a lower annular pedestal 91A and upper annular cap 91B. More particularly, the pedestal 91A has an upward opening, rectangular cross-section, diametral groove (FIG. 9) defining the bottom and side surfaces of the transverse guideway 93, and leaving a pair of transversely opposed, chordal sidewalls 95. The sidewalls 95 here extend slightly above the sides of the transverse guideway 93. Diametrally opposed chordal recesses 96, of small depth compared to the depth of the transverse guideway 93, face upward from and indent the tops 97 of the sidewalls 95 and are here coaxial with the central passage 12 of the head 11.

The annular cap 91B comprises a ring-like body 100 (FIG. 9) from the bottom 102 of which depends a coaxial, reduced diameter, pendent annular flange 101. The pendent annular flange 101 is of diameter to seat snugly in the chordal recesses 96 upward facing from the annular pedestal 91A, in the manner shown in FIG. 10. The bottom portion of the annular flange 101 is coaxially fixed in the chordal recesses 96 by any convenient means, such as laser welding. In this way, the pendent annular flange 101, the top 97, the sidewalls 95, bottom 102, annular body 100 thus define the annular groove 94.

Figure 12:
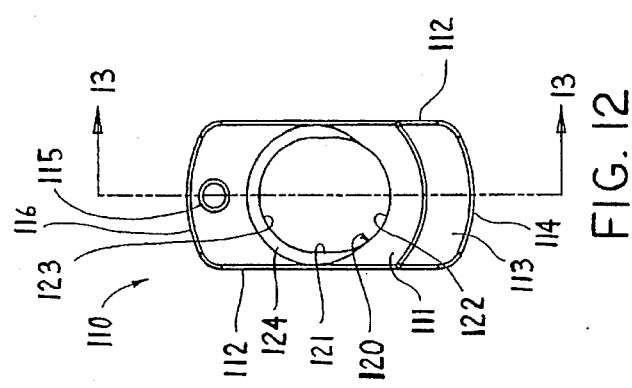
FIG. 12 is a top view of the FIG. 11 locking slider.
Figure 13:
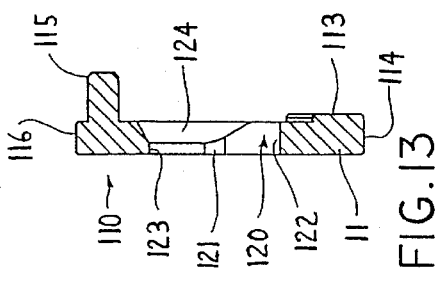
FIG. 13 is a central cross-sectional view substantially taken on the line 13—13 of FIG. 12.
Figure 11:
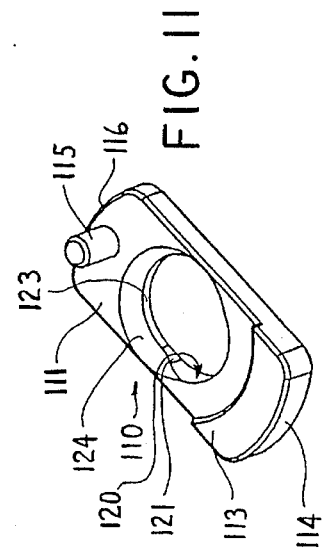
FIG. 11 is a pictorial view of the FIG. 9 locking slider.

The lock unit 90 further comprises a generally rectangular slider 110 (FIGS. 9–13). The slider 110 here comprises a plate-like member 111 (FIGS. 9 and 11–13) having parallel sides 112, a raised shoulder 113 at a manually pushable end 114 thereof and an upstanding post 115 at the other end 116 thereof. A through hole 120 extends through the central portion of the plate-like member 111 and is spaced between the shoulder 113 and post 115. The hole 120 is oblong and its length direction and its parallel sides 121 (FIG. 12) parallel the parallel sides 112 of the plate-like member 111. The rounded ends 122 and 123 of the hole 120 are spaced inboard of the shoulder 113 and post 115, respectively. The upper edge of the hole 120 is beveled at 124 (FIGS. 11–13). The bevel 124 is, as seen from the top in FIG. 12, generally U-shaped in plan, extending from the rounded end 123 of the hole 120 around into the opposite sides 121 thereof.

The plate-like member 111 (FIG. 9) is of width and thickness, between the raised shoulder 113 and upstanding post 115, to fit snugly but diametrally slideably in the transverse guideway 93, as seen for example in FIGS. 6–8 and 10, with the annular cap 91B fixed atop the annular pedestal 91A.

The slider 110 is installed in the lock carrier 90 as follows. Prior to dropping of the annular cap 91B into the chordal recesses 96 in the tops of the pedestal sidewalls 95, the slider 110 is dropped into the upfacing groove defined between the sidewalls 95 of the pedestal 91A. Fixing of the annular cap 91B (FIGS. 9 and 10) atop the annular pedestal 91A, as above-described, traps the central portion of the slider 110 axially between the annular pedestal 91A and annular cap 91B, namely for snug diametrally transverse sliding movement in the transverse guideway 93. The raised shoulder 113 and upstanding post 115 positively prevent the slider 110 from sliding rightwardly or leftwardly, respectively, out of the transverse guideway 93, as seen for example in FIGS. 7 and 8, by radial interference with the pendent annular flange 101 of the annular cap 91B.

In the preferred embodiment shown, an upstanding, radially outward facing notch 125 (FIGS. 7 and 15) extends up through the height of the pendent annular flange 101 and partly up into the overhanging annular body 100 of the annular cap 91B to partially receive the upstanding post 115 of the slider 110. Thus, the annular cap 91B has a required circumferential orientation in which it is to be fixed upon the pedestal 91A, namely so that the notch 125 opposes the upstanding post 115 of the slider 110, as shown in FIG. 15.

An elastically circumferentially stretchable, annular tension spring member 130 (FIG. 9) conveniently comprises a conventional elastomeric O-ring 130 (FIGS. 7-10). Once the annular cap 91B has been fixed atop the annular pedestal 91A, with the slider 110 trapped therebetween, as shown in FIG. 10, the O-ring 130 is stretched enough to slide or roll it down over the annular body 100 (FIG. 10) and allow it to snap elastically into the annular groove 94 into circumferentially tension surrounding relationship with the pendent annular flange 101 and upstanding slider post 115, as seen in FIGS. 8 and 15. The O-ring 130 thus firmly resiliently holds the slider 110 in its leftwardmost (FIG. 6) rest position with the upstanding post 115 of the slider pressed into the notch 125 and the shoulder 113 spaced leftwardly away from the pendent annular flange 101 of the annular cap 91B, so that the manually pushable end 114 of the slider protrudes its maximum amount radially from the cannula head 11 as seen in FIG. 6 and 15. By manually pushing the end 114 of the slider 110 rightwardly (FIG. 6) toward the central axis of the head 11, the slider 110 can be displaced rightwardly to its FIG. 7 position in which the upstanding pin 115 of the slider is pushed at least partly out of its notch 125 to further diametrally stretch the O-ring 130. Upon release of rightward pressure on the end 114 of the slider, the O-ring 130 resiliently but firmly returns the slider 110 leftwardly from its FIG. 7 to its FIGS. 6 and 8 position.

The outer edges of the body 100 of the annular cap 91B are preferably beveled (as at 126 in FIG. 10) to assist passing the stretched O-ring 130 downward over the body 100 and into the annular groove 94 without damage to the O-ring 130.

The spacing between the shoulder 113 and post 115 exceeds the diametral width of the pendent annular flange 101, as measured from the bottom of the notch 125 diametrally to the opposite side of the pendent annular flange 101, to permit sufficient diametral sliding displacement of the slider for the locking and unlocking functions hereafter described.

The top of the upper portion 40 of the central passage 12 opens through the top of the annular cap 91B and is bevelled at 133 (FIG. 6) to facilitate entrance of the bottom end of a tool (for example the bottom end 60 of a tool 50 in FIG. 2) down into the widened upper portion 40 of the central passage 12 of the head 11.

A variety of tools can be inserted forwardly (downwardly in FIG. 6) into the proximal end of the head 11 of the cannula 10. The tools 50, 51 and 52 of FIGS. 2–4 are examples. The insertion process is similar regardless of the specific tool. In the embodiment shown in FIGS. 6–8 assume the trocar 50, for example, is being inserted. Thus, the bottom end 60 of the trocar can be led downward past the bevel 133 and into the widened upper portion 40 of the central passage 12 of the cannula 10. The elongate rod 53 of the tool 50 passes down through the head 11 and down into the tube 13 as shown in FIG. 6. The bottom end 60 of the tool 50 clears the internal O-ring seal 82 easily as it passes downward therethrough, so as not to injure said O-ring. The taper 41 guides the bottom end 60 of the tool 50 into the narrowed lower portion 42 of the cannula central passage 12 and thence down into the tube 13 of the cannula 10.

Continued insertion of the tool 50 into the cannula 10 brings the rounded taper 58 forward close to the entry bevel 133 of the proximal end of the upper portion 40 of the central passage 12 as shown in FIG. 6. Continued downward (forward) movement of the tool passes the taper 58 down into the annular cap 91B and through the oblong hole 120. The tool taper 58 engages the slider bevel 124 and cams the slider 110 rightwardly against the circumferential tension of the resilient O-ring 130, thereby stretching the O-ring 130 as the slider post 115 moves rightward to its FIG. 7 unlock position. Continued downward (forward) movement of the tool 50 moves the lower portion of the cylindrical tool portion 56 below the annular lock groove 57 into downward sliding contact with the rightward end 123 of the slider hole 120 as seen in FIG. 7, to hold the slider 110 in its rightward, unlock, FIG. 7 position.

The tool taper 58 continues downward into the O-ring seal 82. The rounded bottom end 59 of the taper 58 prevents it from injuring the O-ring 82 as it passes downward thereinto. Continued downward movement of the taper 58 past the O-ring seal 82 presses the O-ring seal 82 radially outward to bring the lower cylindrical portion 56 of the tool into sealing contact with the O-ring 82, pressing same radially outward against the surrounding material of the pedestal 91A, as seen in FIG. 8.

As the lower cylindrical portion 56 of the tool moves down past the slider 110, the annular lock groove 57 of the tool, due to its reduced diameter, allows the O-ring 130 to resiliently pull the slider 110 back to its leftward, unlock position as shown in FIG. 8, wherein the rightward end 123 of the slider oblong hole 120 enters the annular lock groove 57 and overlies the lower cylindrical portion 56 of the tool to positively mechanically block upward movement of the tool 50 out of the cannula 10. In the embodiment shown, the handgrip 55 of the tool 50 comes to rest upon the top of the annular cap 91B as the lower cylindrical portion 56 of the tool 50 drops slightly below the slider 110 and transverse guideway 92 as shown in FIG. 8.

The tool 50 is thus fully installed in its use position within the cannula 10.

To remove the tool 50 from the cannula 10 requires a reversal of the above described installation process. Removal of the tool 50 is started by pressing upward (in FIG. 8) against the radially enlarged handgrip 55 of the tool, while pressing rightward against the manually pushable end 114 of the slider 110 to shift the slider 110 rightward, against the resilient force of the O-ring 130, beyond its FIG. 7 unlock position. With the slider 110 slightly to the right of its FIG. 7 position, the slider clears the top of the lower cylindrical portion 56 of the tool 50, allowing the upward force on the tool handgrip 55 to move the tool upward to its FIG. 7 position, wherein the tool annular groove 57 is raised above the slider 110.

If desired, the above operation can be carried out with one hand, namely by gripping the proximal portion 80 of the cannula 10 with the fingers and palm, while pushing with the thumb simultaneously upward on the under side of the radially enlarged hand grip 55 of the tool and rightward on the manually pushable end 114 of the slider 110, to displace the slider rightwardly past its FIG. 7 position and then the tool upward, as above discussed. Thus, one handed unlocking of the tool 50 from the cannula 10 can readily be accomplished.

Thereafter removal of the tool 50 from the cannula 10 is accomplished simply by pulling the tool 50 upwardly from its FIG. 7 position past its FIG. 6 position. In this way, any desired series of tools can be inserted and removed, in sequence, with respect to the cannula 10.

While a given tool, such as the tool 50, is in its fully inserted, locked, FIG. 8 position in the cannula 10, the seal O-ring 82 is radially pressed between the lower cylindrical portion 56 of the tool and the radially outer wall of its annular groove 81 (FIG. 8) in the pedestal 91A, which provides a tight fluid pressure seal between the tool 50 and cannula 10 to prevent upward loss therepast of fluid, such as pressure gas, from the operating site in which the lower end of the cannula 10 is located.

The present invention thus provides an inexpensive, simple, yet reliable axial locking and sealing of a tool within a cannula.

In the preferred embodiment shown, a notch 140 (FIGS. 6 and 14) indents the top of the annular pedestal cap 91B. The notch 140 opens upward and is of substantially rectangular cross-section as seen in FIG. 6 and is of substantially rectangular plan as seen in FIG. 14. The notch 140 is preferably of horizontal width (chordal width) about equal to the diameter of the upper portion 40 of the cannula central passage 12, into which it radially opens. The axial depth of the notch 140 is, in the preferred embodiment shown, about half the actual thickness of the body 100 of the annular cap 91B. The notch 140, in the preferred embodiment shown, extends diametrally opposite the notch 125 which receives the slider post 115.

Although it is not necessary to circumferentially locate some tools, such as the trocar 50 and obturator 51, it is desirable to rigidly circumferentially locate other tools, such as the scope 52. It is for this purpose that the notch 140 is provided in the cannula 10. More particularly, a tool to be positively circumferentially located in the cannula 10, such as the FIG. 4 scope 52, is provided with a radially protruding, plate-like key 143, shaped and sized to fit easily but snugly in the groove 140 when the tool 52 is fully installed in the cannula, as shown in FIG. 8A, and like the tool 50 in FIG. 8. The key 143 is here provided on the underside of the viewing barrel 71, where it radially protrudes from the upper circumferential portion 56B from which the viewing barrel 71 is upstanding. Thus, in the embodiment shown, with the viewing barrel 71 of the tool 52 resting atop the annular cap 91B, circumferential interference between the notch 140 and key 143 positively prevents rotation of the tool 50 with respect to the cannula 10. The opposed edges 144 and 145 (FIG. 8A) of the notch 140 and key 143, respectively, are preferably beveled to facilitate downward entry of the key 143 into the notch 140 upon rotating the tool with the key 143 resting atop the annular cap 91B.

The cannula 10 above disclosed may be sized to receive tools used with prior cannula systems, for example of the kind shown in above mentioned U.S. Pat. No. 5,171,245 assigned to the Assignee of the present invention, namely tools provided with a taper, lower cylindrical portion, annular groove, and upper cylindrical portion generally like those shown at 58, 56, 57, 56 in FIG. 2.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. An endoscopic surgery cannula insertable into a surgical site in a patient for coaxially slidably receiving an endoscopic surgical tool, the cannula comprising:

a distal portion insertable into proximity with a surgical site in a patient;

a proximal portion accessible to surgical personnel for receiving an endoscopic surgical tool, said cannula having an axial through passage extending through the proximal and distal portions thereof for receiving a surgical tool, said proximal portion comprising lock means transversely slidable on said cannula proximal portion for entering said passage and interfering with axial movement of a tool therein, and elastomeric loop means surrounding said cannula proximal portion and lock means for resiliently urging said lock means transversely toward said passage for interfering with axial movement of a tool in such passage, said elastomeric loop means being stretchable to allow transverse movement of said locking means out of interfering relationship and with respect to said passage.

2. The apparatus of claim 1 including a transverse guideway on said cannula, said lock means comprises a slider captive in said guideway and slidable therein transversely of said cannula, said slider having a tool engaging edge facing said passage in said cannula and slidable into said passage to engage and axially lock a tool with respect to said cannula, means on said slider engageable by said elastomeric loop means for urging said edge away from said passage.

3. The apparatus of claim 1 including a diametral through slot on said proximal portion of said cannula said lock means comprising a rigid slider plate slidable in said diametral slot, said plate having an oblong axial through-hole registerable with said cannula passage, said through-hole having a transverse width at least as large as the diameter of the adjacent portion of the cannula passage and having a length dimension, parallel to the length of the through slot, exceeding said diameter of said cannula passage, said slider having an axial protrusion on one end thereof, said slider having a tool engaging edge at one end of said through-hole adjacent to said protrusion, said elastomeric loop means comprising a stretchable ring surrounding said cannula and said protrusion of said slider for resiliently urging said slider in a direction to move said tool engaging edge toward from said cannula passage.

4. The apparatus of claim 3 in which said cannula has an annular groove in the peripheral wall thereof axially adjacent said slider, said stretchable ring comprising an O-ring snap fitted into said annular groove, said protrusion protruding axially into said annular groove and bearing on the inside surface of said O-ring, said slider having a manually engageable end normally protruding radially from said cannula slot and substantially diametrally opposite the location of said protrusion on said slider, such that manual pushing on said manually engageable end of said slider urges said tool engaging edge out of said passage and urges said protrusion radially outward to stretch said O-ring, said O-ring resiliently urging said slider in the opposite direction, namely to push the slider protrusion and tool engaging edge radially inward with respect to said cannula and push said manually engageable end of said slider radially outward beyond the opposite side of the cannula to a rest position.

5. The apparatus of claim 1 including a notch in the proximal end wall of the cannula, said notch facing radially into the proximal end of the cannula passage and having surface means for engaging a circumferential locking key on a tool to be inserted into the cannula passage for circumferentially locking such tool with respect to the cannula.

6. The apparatus of claim 1 including a seal ring facing radially into said passage axially inboard of said lock means for preventing gas escape along a tool in said passage locked in said passage by said locking means.

7. The apparatus of claim 1 including an elongate tool insertable in said through passage from the proximal portion thereof to reach a surgical site, said tool comprising a taper for transversely slideably displacing said lock means on said cannula, said tool having groove means spaced proximally from said taper and permitting entry thereinto of said lock means in response to contraction of elastomeric loop means to axially lock the tool in said passage.

8. The apparatus of claim 7 in which said cannula includes a seal ring facing radially into said passage axially inboard of said lock means for preventing gas escape along said tool when locked in said passage by said locking means, said seal ring being engageable and expandable by said taper on said tool during insertion of said tool in said cannula, said taper being free of sharp edges that might damage said seal ring, said tool including a cylindrical portion between said taper and said groove for sealing engagement with said seal ring.

9. An endoscopic surgery cannula insertable into a surgical site in a patient for coaxially slideably receiving an endoscopic surgical tool, the cannula comprising:

a distal portion insertable into proximity with a surgical site in a patient;

a proximal portion accessible to surgical personnel for receiving an endoscopic surgical tool, said cannula having an axial through passage extending through the proximal and distal portions thereof for receiving a surgical tool, said proximal portion comprising lock means transversely slidable on said cannula proximal portion for entering said passage and interfering with axial movement of a tool therein and elastomeric means for urging said lock means into interfering relation with a tool in such passage, said proximal portion comprising a transverse guideway on said cannula, said lock means comprising a slider captive in said guideway and slidable therein transversely of said cannula for locking and unlocking tool with respect to the cannula, said cannula proximal portion comprising an annular pedestal topped by an annular cap fixed thereto in coaxial relation therewith, said transverse guideway being provided axially between said annular pedestal and annular cap, said slider having opposite ends protruding transversely on opposite sides from said transverse guideway, said protruding ends of said slider having axial protrusions fixed thereon for interfering with opposite sides of said cannula proximal portion and thereby for limiting the extent of sliding motion of said slider and preventing in a positive manner any loss of said slider from said transverse guideway, such that the slider is maintained captive on said cannula.

10. The apparatus of claim 9 in which pedestal has a rectangular cross-section, a diametrally extending groove open in the proximal end thereof and opening transversely in opposite directions therefrom, said cap overlying said groove and closing the proximal side thereof to define therewith said transverse guideway for said slider, said pedestal and cap having opposed recess means and means entrant axially in said recess means for positively radially fixing said cap on said pedestal and means for fixing said cap axially on said pedestal.

11. An endoscopic surgery system including a cannula insertable into a surgical site in a patient and an endoscopic surgical tool insertable into said cannula for thereby approaching said surgical site, the system comprising:

a cannula having a distal portion insertable into proximity with a surgical site in a patient;

said cannula further having a proximal portion accessible to surgical personnel for receiving an endoscopic surgical tool, said cannula having an axial through passage extending through the proximal and distal portions thereof for receiving a surgical tool, said proximal portion comprising lock means transversely slidable on said cannula proximal portion for entering said passage and interfering with axial movement of a tool therein, and elastomeric means for resiliently urging said locking means transversely towards said passage for interfering with axial movement of a tool in such passage;

an elongate tool insertable in said passage at said proximal portion of said cannula, said tool comprising a distally facing taper engageable with said lock means for transversely sliding against said elastomeric means to permit entry of said tool through said cannula, said tool further having an annular groove spaced proximally from said taper for receiving said lock means therein to axially lock said tool in said cannula;

means on said tool and cannula and extending radially eccentrically from said cannula passage and interengageable upon completion of insertion of said tool in said cannula for positively blocking relative circumferential movement between said cannula and tool;

a second tool alternatively insertable in said cannula in place of said first mentioned tool, said second tool being free of radial protrusions so as to avoid circumferential locking thereof with respect to said cannula.

12. The apparatus of claim 11 in which said cannula has an upfacing, radially eccentric notch at the proximal end thereof and said first mentioned tool has a down facing radially eccentric key receivable in said notch upon full insertion of said first mentioned tool into said cannula, said notch and key being generally rectangular in plan and of axial thickness sufficient to lock circumferential movement of said tool in said cannula with said key axially received in said notch.

* * * * *